US008241307B2

(12) United States Patent
Benson

(10) Patent No.: US 8,241,307 B2
(45) Date of Patent: Aug. 14, 2012

(54) KNOT TYING LAPAROSCOPIC NEEDLE DRIVER

(76) Inventor: Steven Preston Benson, Greenville, NC (US)

( * ) Notice: Subject to any disclaimer, the term of this patent is extended or adjusted under 35 U.S.C. 154(b) by 625 days.

(21) Appl. No.: 12/395,706

(22) Filed: Mar. 1, 2009

(65) Prior Publication Data

US 2009/0228025 A1 Sep. 10, 2009

Related U.S. Application Data

(60) Provisional application No. 61/068,124, filed on Mar. 5, 2008.

(51) Int. Cl.
*A61B 17/04* (2006.01)

(52) U.S. Cl. ........................................ 606/148; 606/205

(58) Field of Classification Search .................. 606/144, 606/148, 205–208, 222–233
See application file for complete search history.

(56) References Cited

U.S. PATENT DOCUMENTS

| | | | | |
|---|---|---|---|---|
| 5,171,257 | A * | 12/1992 | Ferzli | 606/205 |
| 5,389,103 | A * | 2/1995 | Melzer et al. | 606/144 |
| 5,480,406 | A * | 1/1996 | Nolan et al. | 606/139 |

* cited by examiner

*Primary Examiner* — Tuan Nguyen
*Assistant Examiner* — Thomas McEvoy

(57) ABSTRACT

A modification to a standard needle driver in the form of a deployable and retractable projection at the working end of the needle driver with which the operator can control the suture in order to facilitate tying a knot in the suture. This modification solves the difficult problem of controlling the suture during the rate-limiting step of knot tying allowing for faster, easier knot tying in laparoscopic and single port surgery.

5 Claims, 5 Drawing Sheets

Species 10

1

2

3

6

Species 10

5

Species 20

Species 30
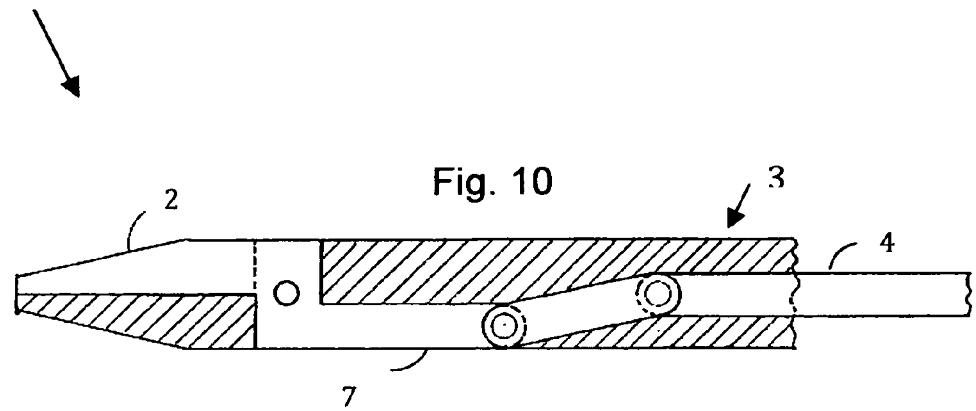
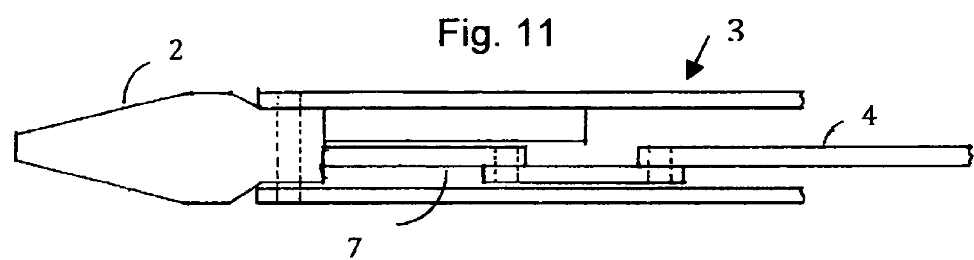
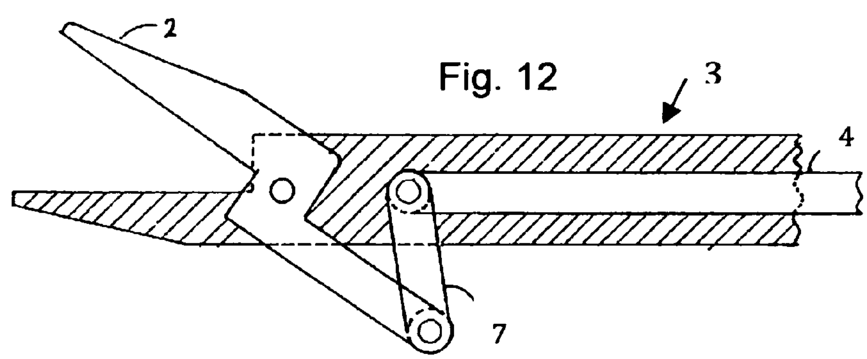

Species 40
Fig.13
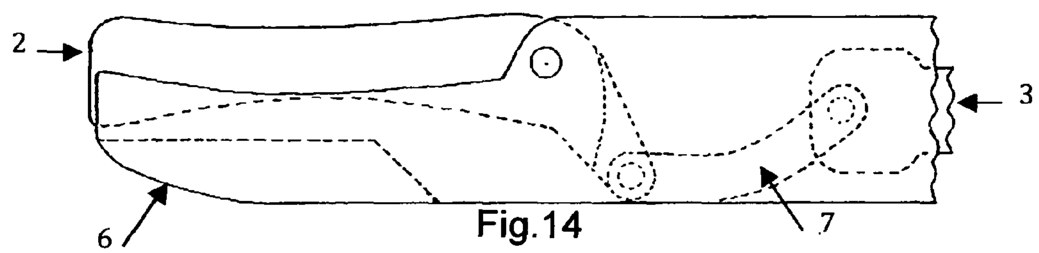
Fig.14
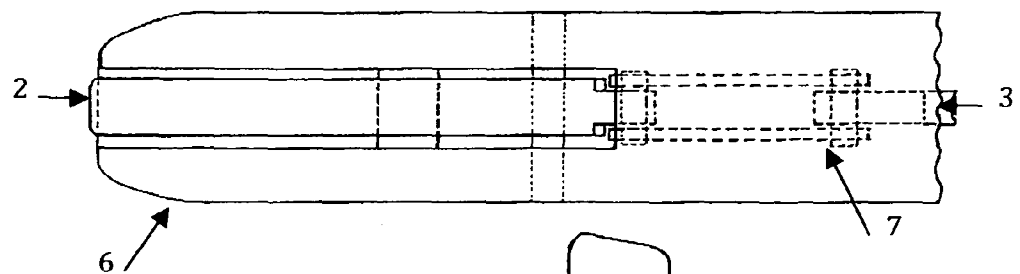
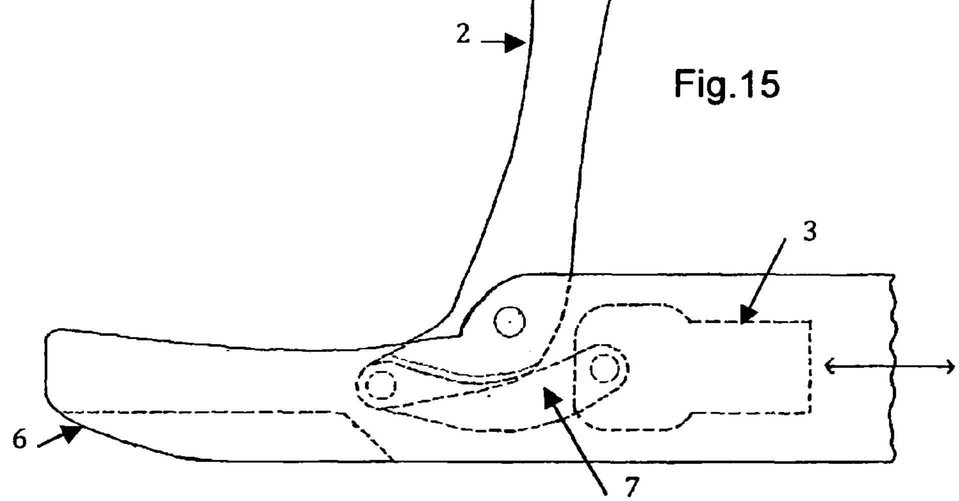
Fig.15

KNOT TYING LAPAROSCOPIC NEEDLE DRIVER

CROSS-REFERENCE TO RELATED APPLICATIONS

Benefit of provisional application 61/068,124 filed Mar. 5, 2008 is claimed.

STATEMENT REGARDING FEDERALLY SPONSORED RESEARCH OR DEVELOPMENT N/A

REFERENCE TO SEQUENCE LISTING, TABLE, COMPUTER PROGRAM N/A

BACKGROUND OF THE INVENTION

The field of endeavor this invention is directed to a surgical instrument and a surgical knot tying aid, including but not limited to laparoscopic surgical knot tying. This instrument and technique will be of immense value in laparoscopic or endoscopic surgery and any surgery requiring tying knots in suture in a deep cavity. Instrument placement often makes knot tying extremely difficult even for the most experienced laparoscopic surgeons. Inexperienced surgeons struggle with learning to knot tie with standard techniques so much so that procedures requiring suturing and knot tying are considered advanced procedures. In laparoscopic surgery instruments are placed into a body cavity filled with gas. The instruments are placed through devices called ports, which allow the instruments to be taken in an out of the body without loss of the insufflated gas. This gas fills the cavity providing room to manipulate instruments and visualize tissues. These ports allow limited movement of the instruments in the body because there is an effective fulcrum at the point in which the skin is breached. This restriction coupled with limited visualization in the body on a flat monitor makes tying knots inside the body (Intracorporeal) very difficult. Typically the smaller the angle between the two instruments being used to tie, the more difficult knot tying becomes. This difficulty is further exacerbated when the cavity in which the surgery is being performed is very small as is the case when placing sutures in the pelvis as would be done in a laparoscopic prostatectomy, or culpopexy. A growing trend in laparoscopic surgery is single port surgery. In single port surgery multiple trocars are placed through a single small skin incision. The advantage is a much better cosmetic result, as there is only one small incision. Natural orifice surgery is another trend in modern laparoscopic surgery that results in no visible skin incision. The drawback of these surgical approaches is that surgical instruments must be introduced into the body very close together. This further restricts a surgeon's ability to manipulate the instruments and therefore increases the difficulty of performing a surgery that would be more easily accomplished with a standard laparoscopic or open approach. This increased difficulty and decreased range of motion of the surgical instrumentation necessitates new instrumentation that can help accomplish surgical tasks under more restrictive conditions. One of the most difficult tasks is intracorporeal knot tying. The modified needle driver and complementary method of use, claimed in this patent application, make knot tying easy and allow for unrestricted port placement. This is of particular advantage in laparoscopic applications where instrument placement is limited, as it is in single port surgery and natural orifice surgery, and in situations where suturing is necessary in small spaces like in the pelvis. With the modified needle driver, a knot can be easily tied even with two instruments placed so close together that they are essentially parallel. This allows for surgery previously requiring open procedures due to the difficult knot tying situations to be performed laparoscopically. In the growing trend in laparoscopic surgery known as single port surgery this modified needle driver will allow the use of standard suture and ligature placement where suturing was previously impossible. This opens possibilities for new procedures to be done with the single-port approach that previously were not possible due to the need for knot-tying.

Standard endoscopic knot tying is accomplished after a stitch has been placed with an instrument called a needle driver. A surgeons knot is formed by multiple square knots tied in a succession of half hitches. Each half hitch is called a throw. A throw is formed with the use of two grasping instruments, typically a needle driver and a tissue grasper or second needle driver. A suture with a curved needle attached to at least one end of the suture is placed through the tissue to be tied using the needle driver in the right hand to manipulate the needle and place it in the desired position. If a ligature is to be placed then an angled grasper is often placed behind the tissue to be ligated and the suture handed with a needle driver to the jaws of the angled grasper and then the suture is pulled behind the tissue. In either case the suture is pulled through the tissue to leave a short suture end of approximately two and a half centimeters and a long end of eight to ten centimeters. The suture is now in a position to form a knot. The long suture is grasped with the instrument in the left hand and then with a difficult combination of moves the long suture is wrapped around the tip of the right hand instrument to form one or two loops around the end of the instrument. The right hand instrument with the loops around the tip must then be used to grasp the short end of the suture. This short end is then pulled through the loops surrounding the tip of the instrument and the ends are pulled in opposite directions to snug the first throw of the knot. The next throw is typically formed in the same manor only with the wraps wound around the right hand instrument in the opposite direction as the wraps in the first throw. Subsequent throws are done in an alternating fashion, which allows the knot to snug down flat forming a square knot, which is more secure. A standard surgeons knot starts with a throw that has two wraps around the instrument because this facilitates the knot holding snug once it is pulled tight on the first throw. Sometimes a slipknot is formed by making two throws in the same direction. This accomplishes the same thing as a surgeons knot, allowing the knot to be secured snugly before locking throws are applied. The rate limiting and most difficult step is wrapping the suture around the tip of the right hand instrument and then keeping the wraps on the tip while maneuvering the instrument into a position to grasp the short end of the suture. To make a double wrap to form a surgeons knot is often impossible however it is often preferable to the slipknot because the slipknot can fail to slip and not allow the suture to be tightened appropriately.

The lap needle driver is typically 14 inches long with a working end comprised of two jaws, which approximate to hold a needle or grasp suture. The large distance between the hand piece and the working end, the reliance on a two dimensional monitor and the restricted movement secondary to ports and port placement make intracorporeal knot tying very difficult.

Many attempts to solve the problem of intracorporeal knot tying have been made. Most are too complex, cumbersome or slow, if they even work at all. Task specific devices such as the endo-stitch have limited applications and are single use as well as expensive. Knot pushers work but have many drawbacks, which keep them from being widely accepted. They require multiple instrument exchanges, which exposes the patient to increased risk of injury. They are slow to tie knots, and require very long sutures to be used, which are not available in all sizes. They increase the risk of tearing the suture out of delicate tissue. Intracorporeal knot tying aids are available but not widely accepted. Like the knot pusher they require multiple instrument exchanges with the added risk. Some advocate additional port sites for the tying aid. This also increases risk to, as well as scaring of the patient. Most surgeons prefer to minimize the number of port sites. Many other knot-tying devices have been patented but are not useful. The following examples illustrate the industry standard for laparoscopic needle drivers and the major differences between the modified needle driver, of claim one and some of the best attempts to improve laparoscopic needle drivers.

U.S. Pat. No. 5,242,458 held by Ethicon, Inc. (Somerville, N.J.) represents the industry standard laparoscopic needle driver. This is a typical design for most needle drivers in use today. It represents a standard jaw design with jaws that open approximately thirty degrees. This angle is not sufficient to control suture while knot tying nor is it designed to be.

U.S. Pat. No. 5,364,409 held by Ethicon, Inc. (Somerville, N.J.). This patent represents the basic laparoscopic needle driver employing a non-deployable shaft based accessory hook to capture suture and assist in tying. The key differences are that the hook is not deployable and retractable nor is it part of the jaw mechanism. This design for a non-deployable hook to aid in knot tying is not useful and is dangerous in practice because the hook would catch on tissue inadvertently. Knot tying with this configuration would be impeded because the hook is not retractable and would hinder the loops sliding off the instrument to form the knot. The hook for catching the suture would also catch on the seal in the trocar, impeding insertion and removal from the body cavity. This requires a second sleeve be employed to cover the hook to keep it from causing damage or impeding insertion and removal through the trocar. This requires added steps to knot tying and causes the instrument to have a wider shaft than the standard five millimeter.

U.S. Pat. No. 5,147,373 represents an attempt to ease knot tying by incorporating a second jaw into the shaft of a grasper or needle driver. This would allow for more control of the suture but the design is unnecessarily complex and would not be applicable to a standard five-millimeter diameter instrument. Other major disadvantages of this design include the necessity of a secondary control mechanism. This would slow the actual knot tying. The design claimed in claim one claims secondary control mechanism however the most useful example is the simplest with the jaw acting as the projection under direct control of the jaw mechanism. This allows the surgeon to focus on the task and not multiple controls. Claim one claims a radial projection to catch the suture as it slides over the shaft as it would be done in a standard knot tying procedure. This differs from any mechanism that would require actually grasping the suture with a secondary grasper of any design. The radial projection is an improvement over a secondary grasping mechanism because it does not require any extra steps be added to the knot tying procedure. The procedure using any secondary grasping mechanism would necessitate multiple added steps. The surgeon would have to release the jaw actuating mechanism, grasp the secondary mechanism, position suture in secondary jaw, grasp suture with secondary mechanism, move hand back to primary jaw mechanism, continue standard knot tying steps, then move hand back to secondary control, release secondary grasper, and finally finish remainder of standard knot tying steps. This is a lot of added complexity and time that is not necessary when using the claimed improved needle driver, which actually decreases the complexity of the knot tying procedure.

U.S. Pat. No. 5,601,578 Endoscopic suturing device 1997 United States Held by Miranic Investments Pty. Ltd. (Geelong, AU) This needle driver is similar in concept except the crucial difference is that the hook is not deployable and retractable. It would get in the way of manipulating the needle and tissue and could potentially be dangerous due to the ease in which tissue could be accidentally hooked and torn, especially while inserting or removing the instrument. The small diameter of the tip of the hook would also make inadvertent puncture of tissue a real and dangerous problem.

Tying knots through a single port approach with current technology is almost impossible. Intracorporeal knot tying is one of the most difficult techniques for laparoscopic surgeons to master and multiple inventions to simplify this difficult task have been designed. They all have one or more major drawbacks. Commonly, they necessitate exchanging instruments in and out of the access ports. This wastes time; increasing the time the patient must be under anesthesia and therefore increases the risk to the patient. Exchanging instruments also poses a risk to the patient by increasing the risk of accidental puncture or damage to other organs or structure during the exchange, as the visualization is difficult and instruments are not always visualized as they are exchanged. Risk of unintended and possibly unnoticed damage is increased with increased instrument exchanges. Another common drawback to knot tying devices is complexity. The more complex a mechanism the more likely it will malfunction. Surgical instrumentation must be reliable and durable. Single use mechanisms are not cost effective and complex mechanisms do not withstand the rigors of multiple washings and sterilization cycles. Many tying devices require set up for each suture or set up with device specific suture. This is once again time consuming and takes special training for surgeon and support staff. The majority of laparoscopic suturing and knot tying is still done with a traditional needle driver, which has not changed much in 40 years. Most surgeons want to tie the knot with the instrument they placed the suture with. They want the knot tying device to be versatile, and familiar. They do not want to have to learn complicated knot tying procedures or to use special suture that must be preloaded or set up for each stitch. Tying knots laparoscopically is difficult and learning how to do it takes a lot of time, practice, and aptitude. Not all laparoscopic surgeons master knot tying. The needle driver of claim one is simple, familiar and requires no new skill sets to be learned.

BRIEF SUMMARY OF THE INVENTION

A modification to a standard needle driver in the form of a deployable and retractable projection, which allows for complete control of suture while laparoscopically tying knots. This modification greatly simplifies and eases knot tying in laparoscopic surgery and opens up possibilities for suturing in single port surgery. The best example of this modification employs a mobile upper jaw, which is controlled with a standard hand-piece but is modified to open to an oblique angle when opened maximally. The lower jaw is stationary.

Advantages:

1. The surgeon is able to tie knots easily without added steps
2. Knot tying is fast
3. There is no complex mechanism to fail 4. The needle driver is familiar to the surgeon because any style of needle driver can be modified to work with this concept
5. No secondary actuating mechanism is necessary
6. Makes knot tying in single port surgery easy
7. No instrument exchange is necessary to knot tie
8. Multiple knots may be formed with the same piece of suture material
9. Both running sutures and interrupted sutures may be placed and tied without need for extra instrumentation
10. Any suture material may be used
11. Suture does not have to be long to allow for tying outside the body as with knot pushers
12. The most delicate sutures may be tied
13. Maximum control over the tension placed on the knot is maintained
14. The movements required for the knot tying procedure are small and stay within the visual field of the surgeon
15. Needle driver is easily fashioned within the standard five-millimeter dimension.

EXPLANATION OF FIGURES

Illustrations are not intended to show all possible variations or limit the scope of invention, only to illustrate possible variations.

FIG. 2 shows detail of instrument tie step one, utilizing said modified needle driver (10) of claim 1 and second needle driver(5).

FIG. 3 shows detail of instrument tie step two, crossing long end of said suture(1) over said modified needle driver (10) of claim 1 to engage deployed said projection.

FIG. 4 shows detail of instrument tie step three, looping the suture around the said instrument(10) in the non-dominant hand.

FIG. 5 shows detail of instrument tie step four, grasping short end of said suture (1) with said modified needle driver (10), and retracting said projection(2).

FIG. 6 shows detail of instrument tie step five, pulling short end of said suture (1) through loop (or loops) formed around said modified needle driver (10).

FIG. 7 shows detail of instrument tie final step, ends of suture (1) are pulled in opposite directions to snug knot. These steps form a single throw. These steps are repeated to form multiple throws.

FIGS. 8, 9 & 13-15. Exemplary variations of invention utilizing upper jaw to form projection on needle driver.

FIG. 8 shows one method by which jaw mechanism may be enabled to open to a wide enough degree to be effective as described invention of claim 1. FIG. 8 shows closed position of mobile upper jaw(2) and fixed lower jaw(6). Jaw mechanism is actuated by sliding of shaft (4), which is actuated by any standard hand-piece (not shown).

FIG. 9 shows open and closed position of jaw mechanism of FIG. 8.

FIGS. 10-12 show one embodiment(20) of linkage actuated non-jaw projection (7) actuated by same mechanism, which actuates opening and closing of grasping jaw.

FIGS. 13-15 show one embodiment of linkage-actuated embodiment of invention with projection formed by upper grasping jaw(2). This also illustrates that the invention may be applied to needle driver designed with "needle righting" jaws.

DETAILED DESCRIPTION OF THE INVENTION

Modification to a standard needle driver or grasper, which allows increased ease and precision of knot tying in standard laparoscopic or endoscopic procedures (here in just referred to as laparoscopic) and allows knot tying in previously impossible situations, for example single port surgery. The procedure for using modified needle driver to form a knot in suture material.

The ideal embodiment of the invention is a laparoscopic needle driver or grasper composed of hand-piece, five-millimeter tubular body, and jaw assembly with one fixed jaw and one mobile jaw. The mobile jaw opens much further than is standard, opening greater than ninety degrees. This upper jaw is the deployable and retractable projection used to control the suture. The jaws are controlled by standard hand-piece allowing for surgeon's personal preference, as there are multiple variations. The hand-piece may be modified by a change of angles and pivot placement such that there is an increase in the distance of the movement of the actuating bar that travels the barrel shaft, allowing for wider opening jaw than is usual. The pivot points and lever length of the jaw mechanism may also be modified to utilize a standard short actuator arm movement but translate that movement into a larger jaw movement.

The modified needle driver is unique because it incorporates deployable and retractable apparatus at the jaw-end, which is a projection from the midline of the central axis of the needle driver. This projection works in such a way as to allow a suture to catch on said projection, during knot tying procedure, which keeps the suture from sliding off the end of the instrument as the suture is wrapped around the instrument. This simplifies the most difficult and rate limiting step of forming a knot in a suture. The projection is actuated by the operator and when not deployed lays in such a way that a suture may easily slide off the end of the instrument without catching during the final step of the knot tying. This is key to the invention as others have designed needle drivers with a permanent projection to control the suture, however it becomes more of a hindrance than help because it is not retractable and causes the suture to hang up during the final step of the knot tie.

Furthermore the projection may be actuated by either the mechanism, which controls the jaws of the needle driver, or by separate control mechanism. The preferred embodiment of the mechanism is incorporated into the jaws designed to hold a needle or tissue. This is accomplished by making one of the jaws of the modified needle driver open much further than is standard. An angle formed between the axial midline and the projection of 90 degrees or greater would give the greatest ease of capturing the suture for knot tying. Mechanism must be fully retractable to allow introduction of endoscopic instrument through access ports and to minimize chance of accidentally hooking tissue and causing harm to the patient.

Figure 1:
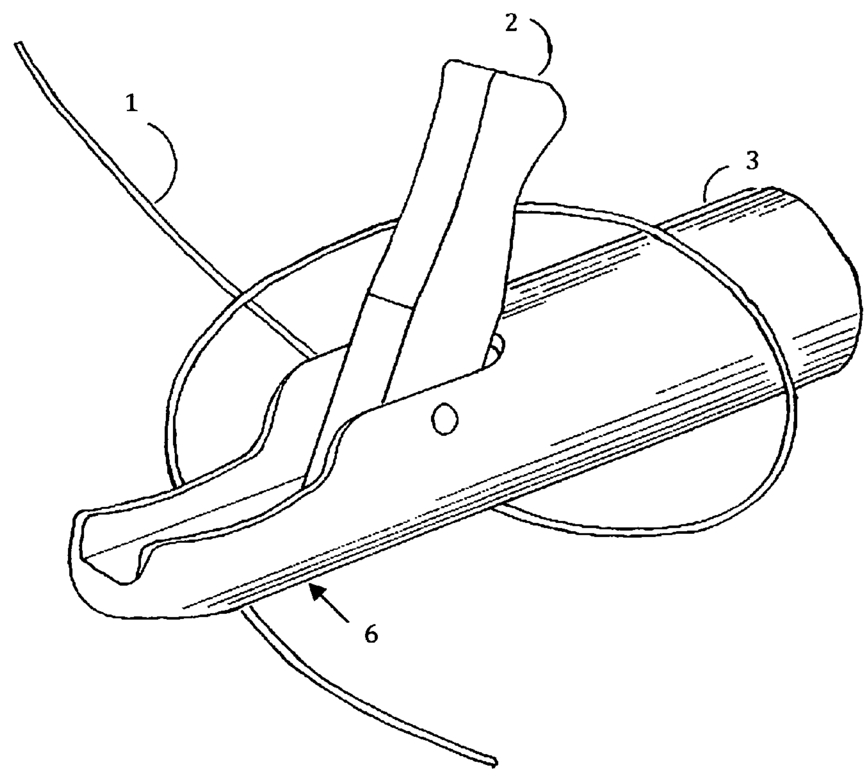
FIG. 1 shows exemplary example of jaw mechanism deployed for knot tying. It shows detail of modified jaw, opening greater than 90 degrees (2), tubular shaft (3), fixed jaw (6) and suture (1).
Figures 2, 3, 4, 5, 6, 7:
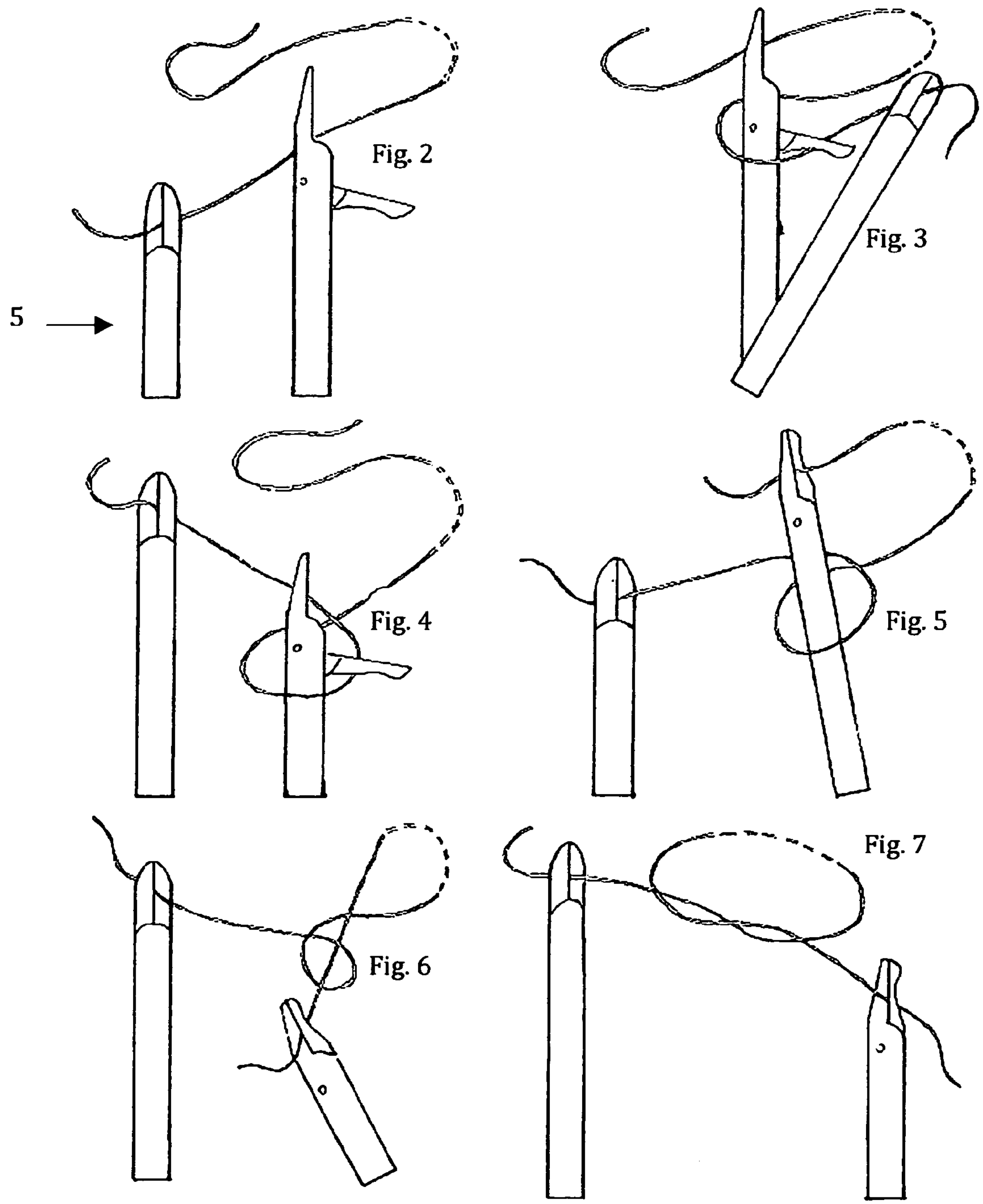
FIGS. 2-7 show illustrations of knot forming technique using modified needle driver.
Figure 8:
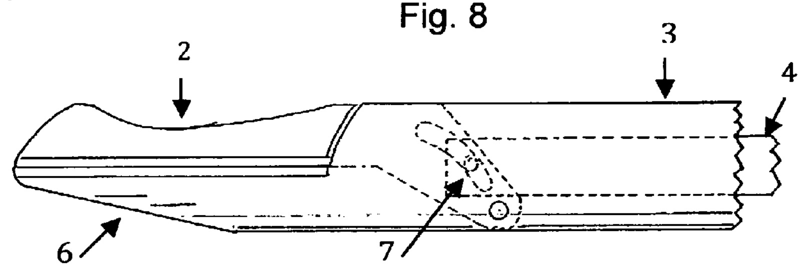
Figure 9:
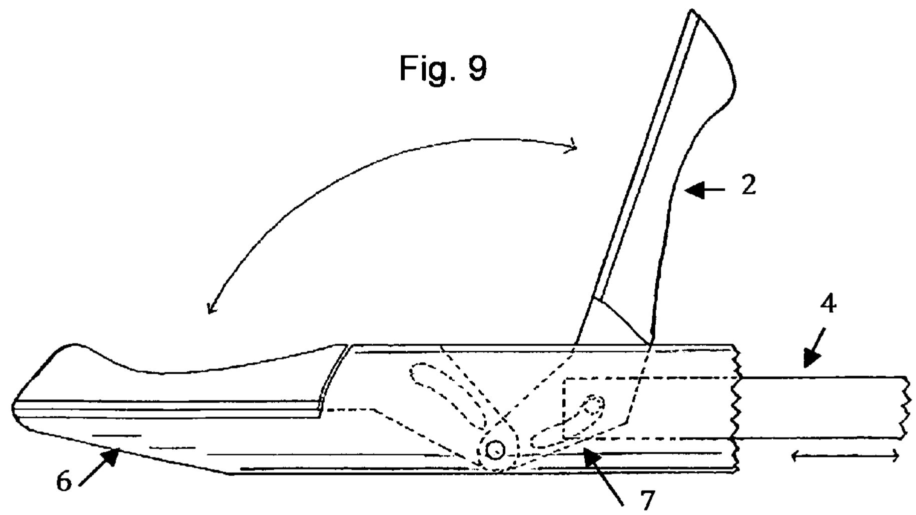

Method for using modified needle driver to perform an instrument-tie. With a standard suture material positioned to tie, start with one end of the suture held in the jaws of a grasper or second needle driver in the operator's non-dominant hand (FIG. 2). The operator then using his/her dominant hand lays the distal end of the modified needle driver on top of the suture being grasped by the non-dominant hand (FIG. 2). With the mechanism deployed on the modified needle driver, the operator then crosses the suture held with the non-dominant hand over top of the shaft of the modified needle driver proximal to the projected mechanism (FIG. 3). This will catch the suture as it slides distally along the shaft of the modified needle driver and allow the suture to easily be looped around the distal end of the instrument (FIG. 4). Multiple loops of suture may be made around the modified needle driver by repeating these steps. The short end of suture may now be grasped by the modified needle driver (FIG. 5). The projection retracts and the short end of suture is pulled through the loop or loops of suture formed around end of modified needle driver, forming one throw of a knot (FIGS. 6&7). To form square knots a second modified needle driver may be used and knot tied by wrapping around the instrument in the non-dominant hand. Additionally, a one-handed square knot may be formed, by alternating direction the loop is placed around the instrument. First placing modified needle driver on top of the suture to form the first throw and then turning the modified needle driver over and placing the suture held by the non-dominant hand on top of the modified needle driver, then crossing underneath with the non-dominant held instrument, catching the suture on the mechanisms projection underneath and easily wrapping around the instrument's end in the opposite direction from the first throw. The two instruments are then used to tighten the knot by pulling the suture ends in opposite direction (FIG. 7). Any standard suture material may be used and may be tied with or without needle attached.

Variation to method utilizing needle driver fitted with rotational shaft. The modified needle driver is placed over suture as described above and suture end is moved across the shaft with the non-dominant hand in such a way that the deployed mechanism can catch the taught suture and pull it around the end of the instrument as it is rotated forming a loop each rotation. The short suture end is then grasped as previously described and the knot is finished as with non-rotational shaft needle driver.

This invention is distinct from other needle drivers because none have ever incorporated a simple deployable and retractable projection to control suture for the purpose of knot tying. Today the typical needle driver opens to approximately 30 degrees, nowhere near the 90 degrees or more needed to maximally control the suture in the ideal embodiment. Standard knot tying methods entail closing the jaws of the needle driver during the rate-limiting step of encircling the suture around the instrument. This new method uses an open jaw or deployed secondary projection to control the suture during this critical step in knot tying.

The invention claimed is:

1. A method of suture knot forming in an anatomical cavity during laparoscopic or endoscopic surgery utilizing a modified needle driver comprising:

a. providing a modified needle driver comprising:
   - a hand piece;
   - a tubular shaft;
   - a sliding shaft axially movable within said tubular shaft;
   - a fixed jaw connected to a distal end of said tubular shaft;
   - a mobile jaw connected to a distal end of said tubular shaft and connected to a distal end of said sliding shaft via a linkage mechanism, wherein said linkage mechanism converts axial movement of said sliding shaft into pivotal movement of said mobile jaw relative to said fixed jaw, wherein said pivotal movement allows said mobile jaw to open from a closed position relative to said fixed jaw to a deployed position having an angle of greater than 90 degrees relative to said fixed jaw and relative to the midline of the central axis of said modified needle driver, wherein a suture may easily slide off said distal end of said tubular shaft when said mobile jaw is in said closed position b. providing, separate from said modified needle driver, a suture with a long end having a needle attached thereto and a short end having no needle attached thereto;

c. providing a second needle driver, separate from said modified needle driver;

d. grasping said long end of said suture with said second needle driver in a non-dominant hand;

e. placing said modified needle driver on top of said suture held by said second needle driver in said non-dominant hand;

f. actuating said slidable shaft to pivot said mobile jaw to said deployed position;

g. while holding said suture long end with said second needle driver, crossing said second needle driver over said tubular shaft, proximal to said mobile jaw in said deployed position;

h. using said second needle driver, looping said suture around said distal end of said tubular shaft in a first direction to form a loop with said suture while said mobile jaw is in said deployed position, thereby preventing said suture from sliding off said tubular shaft;

i. grasping said short end of said suture with said modified needle driver between said fixed jaw and said mobile jaw;

j. with said modified needle driver, pulling said suture through said loop made around said distal end of said tubular shaft to form a first throw of a first knot;

k. pulling said long end and said short end longitudinally apart with both said modified needle driver and said second needle driver to tighten said first throw of said first knot;

I. repeating steps d through k one or more times to form one or more additional throws of said first knot, wherein said one or more additional throws may be formed using said first direction or a second direction, opposite to said first direction to form a locking throw, wherein if two consecutive throws are formed in said first direction then a slipknot is made which allows said suture to be snugged down before a locking throw is made in said second direction.

2. The method of claim 1 wherein said modified needle driver may be adapted to but not limited to:

laparoscopic, endoscopic, microsurgical, arthroscopic, or general surgery use.

3. The method of claim 1 wherein said angle of said mobile jaw is an angle sufficient to control said suture.

4. The method of claim 1 wherein said linkage mechanism provides a pivot point and mechanical stops which can be altered as necessary to accommodate other jaw styles.

5. The method of claim 1 wherein said mobile jaw is constructed and said angle of said deployed position is selected so that inadvertent entrapment of said suture is avoided.

* * * * *